United States Patent [19]

Koppes et al.

[11] Patent Number: 5,194,535
[45] Date of Patent: Mar. 16, 1993

[54] PROCESS FOR PRODUCTION OF ALKADIENE-BASED POLYMER OF INCREASED VINYL CONTENT

[75] Inventors: Margaretha J. C. M. Koppes; Johannes C. M. van der Arend, both of Amsterdam, Netherlands

[73] Assignee: Shell Oil Company, Houston, Tex.

[21] Appl. No.: 894,137

[22] Filed: Jun. 4, 1992

[30] Foreign Application Priority Data

Jun. 10, 1991 [GB] United Kingdom ................. 9112419

[51] Int. Cl.$^5$ ................................................ C08F 4/46
[52] U.S. Cl. .................................... 526/181; 526/173; 526/335; 526/340; 525/250; 525/258
[58] Field of Search ....................... 526/173, 181, 340; 525/258

[56] References Cited

U.S. PATENT DOCUMENTS

| | | |
|---|---|---|
| 3,070,574 | 12/1962 | Kastning et al. ................ 526/181 X |
| 3,288,872 | 11/1966 | House . |
| 3,580,895 | 5/1971 | Onishi et al. . |
| 3,829,409 | 8/1974 | Sommer et al. . |
| 4,554,334 | 11/1985 | Yuki et al. ........................... 526/177 |
| 4,591,624 | 5/1986 | Hall ..................................... 526/177 |
| 5,112,929 | 5/1992 | Hall ..................................... 526/181 |

OTHER PUBLICATIONS

R. H. DeWolfe, "Carboxylic Ortho Acid Derivatives", Academic Press, New York and London, 1970.

*Primary Examiner*—Fred Teskin

[57] ABSTRACT

An improved process for the production of conjugated alkadiene-based polymers of higher vinyl content employs as a structure modifier a compound of the formula

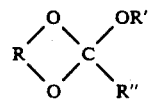

wherein R is alkylene, R' alkyl and R" is hydrogen or hydrocarbyl.

14 Claims, No Drawings

PROCESS FOR PRODUCTION OF ALKADIENE-BASED POLYMER OF INCREASED VINYL CONTENT

FIELD OF THE INVENTION

This invention relates to a process for the production of polymers based on at least one conjugated alkadiene. More particularly, the invention relates to such a process incorporating an improved structure modifier.

BACKGROUND OF THE INVENTION

The process of producing a polymer based on conjugated alkadiene is well known in the art. Such processes are typically conducted in the presence of a hydrocarbon reaction diluent and an organolithium initiator. In the polymerization of conjugated alkadiene, two types of polymerization take place. In what is conventionally termed 1,2 polymerization (or alternatively 3,4 polymerization), the polymerization involves only a single carbon-carbon double bond. The resulting polymer chain includes the carbon atoms of that bond and contains a pendant vinyl group. The extent to which such polymerization takes place is measured by the proportion of such vinyl groups in the polymer and is conventionally referred to as vinyl content. In what is termed 1,4 polymerization, all four carbon atoms of the conjugated system are incorporated into the polymer chain which then includes ethylenic unsaturation.

The vinyl content of polymers formed from conjugated alkadiene is on the order of 10% unless steps are taken to increase the proportion. It is often desirable from consideration of polymer properties to have higher vinyl contents, even as high as contents on the order of 60%. Increased vinyl content is achieved by well known methods through the use of a structure modifier to alter the proportions of 1,2 and 1,4 polymerization of an alkadiene.

One group of widely used structure modifiers is the group of acyclic polyethers such as diethylene glycol dialkyl ether or alkyl orthoesters. However, these modifiers are not entirely satisfactory. The diethylene glycol dialkyl ethers, e.g., diethylene glycol dimethyl ether, have insufficient stability during polymerization and provide protic or other polar derivatives which tend to prematurely terminate polymerization. The ortho esters, such as those disclosed by Onishi et al, U.S. Pat. 3,580,895, appear to decompose during the steam coagulation by which the polymer is conventionally recovered. The decomposition products are observed in the recovered hydrocarbon reaction diluent which must be purified for most efficient use if the diluent is recycled.

A second group of structure modifiers comprises cyclic ethers including cyclic polyethers. Acyclic monoether, i.e., tetrahydrofuran, is known to be relatively ineffective unless used in high concentration. Some cyclic polyethers containing a—linkage, e.g., dioxolane and paraformaldehyde, are described by House, U.S. Pat. No. 3,288,872. Such cyclic polyethers, however, tend to inhibit organoalkali metal initiated polymerization.

It would be of advantage to provide a process for conjugated alkadiene-based polymerization using an improved structure modifier.

SUMMARY OF THE INVENTION

The present invention provides an improved process for the production of conjugated alkadiene polymers of relatively high vinyl content. More particularly, the present invention provides such a process which incorporates an improved cyclic polyether structure modifier of the formula

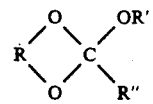

wherein R is a divalent alkylene group of up to 10 carbon atoms inclusive with from 2 to 4 carbon atoms in the bridge, R' is alkyl of up to 10 carbon atoms inclusive and R" is hydrogen or a hydrocarbyl group of up to 1? carbon atoms inclusive.

DESCRIPTION OF THE INVENTION

The present invention is an improved method for producing conjugated alkadiene-based polymers of relatively high vinyl content in the polyalkadiene portion thereof. The conjugated alkadiene useful in the process of the invention has up to 10 carbon atoms inclusive and two conjugated carbon-carbon double bonds. Such compounds are llustrated by the formula

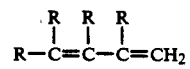

wherein R independently is hydrogen or alkyl. Illustrative of such alkadienes are 1,3-butadiene (butadiene), 2-methyl-1,3-butadiene (isoprene), 1,3-pentadiene, 2,3-dimethyl-1,3-butadiene, 1,3-octadiene and 2,4-dimethyl-1,3-hexaadiene. The preferred alkadienes are butadiene and isoprene, particularly butadiene.

The process of the invention applies to the homopolymerization of the conjugated alkadienes, e.g., the polymerization of butadiene to polybutadiene or the polymerization of isoprene to polyisoprene, as well as to the copolymerization of the conjugated alkadiene with other anionically polymerizable monomers, particularly vinylaromatic hydrocarbons such as styrene and styrene homologs of up to 10 carbon atoms inclusive, e.g., p-methylstyrene, p-ethylstyrene, m-isopropylstyrene, α-methylstyrene and α,4-dimethylstyrene. The copolymerization of alkadiene and vinylaromatic hydrocarbon is suitably random as in the production of random styrene-butadiene copolymers, or is suitably a block polymerization, both of which polymerizations are broadly well known and conventional. The form and structure of block copolymers of vinylaromatic hydrocarbon and conjugated alkadiene are also well known in the art. Illustrative block copolymers are linear polymers such as sequentially-produced copolymer having a block of polymerized vinylaromatic hydrocarbon, a block of polymerized conjugated alkadiene and a second block of polymerized vinylaromatic hydrocarbon. In a second embodiment, the block copolymer is produced by polymerizing a block of polymerized vinylaromatic hydrocarbon and then a block of polymerized conjugated alkadiene. Without deactivating the polymeric species, the "living" polymer is then coupled to produce the block copolymer. Coupling with a difunctional coupling agent results in formation of a linear polymer whereas use of a polyfunctional coupling agent results in production of polymer types known as "star", "radial", or "branched". The formation of these types of block polymer is well known and understood in the art.

The polymerization of the conjugated alkadiene-based polymers is conducted under polymerization conditions in the presence of a hydrocarbon reaction diluent and an organoalkali metal polymerization initiator. The hydrocarbon reaction diluents usefully employed in the polymerization process has from 4 to 10 carbon atoms inclusive and is aliphatic including cycloaliphatic, or aromatic. Illustrative hydrocarbon reaction diluents include n-hexane, n-heptane, cyclopentane, cyclohexane, 2,2,4-trimethylpentane, benzene, toluene and mixtures thereof. The preferred hydrocarbon reaction diluents are cycloaliphatic hydrocarbon reaction diluents, particularly cyclopentane and cyclohexane. Especially preferred is cyclohexane. The hydrocarbon reaction diluent is employed in an amount of at least 100 parts by weight per 100 parts per weight of monomer and preferably in a quantity from about 200 parts by weight to about 1500 parts by weight per 100 parts by weight of conjugated alkadiene monomer.

The organoalkali metal polymerization initiator is suitably an organo compound of an alkali metal, e.g., lithium, sodium or potassium, wherein the organo portion is hydrocarbyl of from 1 to 20 carbon atoms inclusive. Aliphatic, including cycloaliphatic, or aromatic compounds of lithium are preferred such as methyllithium, ethyllithium, n-butyllithium, sec-butyllithium, phenyllithium and naphthyllithium. Particularly preferred is sec-butyllithium. The organoalkali metal polymerization initiator is employed in a quantity from about 0.005 mol to about 1.0 mol per mol of monomer. The preferred quantity of organoalkali metal polymerization initiator is from about 0.05 mol to about 0.1 mol per mol of monomer.

The polymerization of conjugated alkadiene as such or in the preparation of a random or block copolymer incorporating conjugated alkadiene is conducted under polymerization conditions. Such conditions include a polymerization temperature of from about 10° C. to about 100° C., preferably from about 30° C. to about 80° C. The polymerization pressure is sufficient to maintain the reaction mixture in the liquid phase. Ambient pressure is typically employed.

When conjugated alkadiene is being polymerized, the structure of the resulting alkadiene moieties of the resulting polymer is modified to produce polymer of a higher vinyl content by the inclusion within the reaction mixture of a structure modifier of the formula

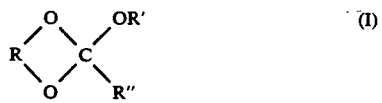

wherein R is a divalent alkylene bridging group of up to 10 carbon atoms inclusive with from 2 to 4 carbon atoms inclusive in the bridge, R' is alkyl of up to 10 carbon atoms inclusive and R" is hydrogen or hydrocarbyl of up to 10 carbon atoms inclusive. Illustrative R groups include 1,2-ethylene, 1,3-propylene, 1,4-butylene, 1,2-propylene, 1,3-butylene and 1,2hexylene. The preferred R group is 1,4-butylene. Illustrative R' groups are methyl, ethyl, propyl and octyl, but the preferred R' group is ethyl. R" is suitably hydrogen or an alkyl group such as methyl, ethyl, hexyl or octyl or an aryl group such as phenyl, tolyl or naphthyl. The preferred R" is methyl, and the preferred compound of the above formula I is 2-ethoxy-2-methyl-1,3-dioxacyclohexane. The structure modifiers of the above formula I are produced by known methods including that disclosed by DeWolfe, "Carboxylic Ortho Acid Derivatives", Academic Press, 1970, and by Narain et al, Indian J. Chem., Sect. B, 17 B, 189-191. The compound 2-ethoxy-2-methyl-4-ethyl-i,3-dioxolane is believed to be novel.

The structure modifier is provided in an amount from about 10 ppm to about 1000 ppm based on total weight of monomer and diluent. Preferably, the amount of structure modifier used is from about 50 ppm to about 850 ppm on the same basis.

The polymerization is conducted by contacting the conjugated alkadiene and any other species to be incorporated into the conjugated alkadiene-based polymer in the presence of the hydrocarbon reaction diluent, the organoalkali metal polymerization initiator and the structure modifier as above described. The mixture is maintained under polymerization conditions until polymerization is complete and the resulting polymer, after deactivation as by treatment with acid, is recovered by conventional methods as by steam distillation removal of reaction diluent and structure modifier. The presence of the structure modifier in the polymerization mixture results in formation of a polymer of higher vinyl content, i.e., a polymer wherein an increased proportion of conjugated alkadiene moieties result from 1,2 polymerization relative to the polymer produced in the absence of the structure modifier. Moreover, the structure modifier remains relatively stable during polymerization and polymer recovery and is suitably recycled together with the hydrocarbon reaction diluent.

The polymer products are materials of established utility and are used as such or in blends with other polymers in applications such as footwear and adhesives.

The invention is further illustrated by the following Illustrative Embodiments which should not be construed as limiting the invention.

Illustrative Embodiment I

The compound 2-ethoxy-2-methyl-4-ethyl-1,3-dioxolane was prepared by heating at 110° C. a mixture of 16.2g (0.1 mol) triethylorthoacetate and 9.5g (0.105 mol) 1,2-butanediol with a catalytic amount of p-toluenesulfonic acid in a reaction flask equipped with a condenser and a Dean-Stark trap. After the collection of more than 10 ml of ethanol over an approximately 2-hour period, the resulting residue was purified by distillation.

The yield of product was 7.2g of colorless liquid, b. pt. 168° C. The $^1$H-NMR spectra were consistent with the structure 2-ethoxy-2-methyl-4-ethyl-1,3-dioxolane.

Illustrative Embodiments II–XI

A series of polymerizations was conducted by introducing into a 500 serum bottle 100 ml of cyclohexene, 12g of butadiene and varying amounts of a structure modifier of the formula

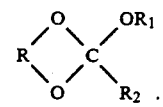

After the bottle contents were homogenized, they were heated to 50° C. in an oil bath. Subsequently, 0.5 mmol of sec-butyllithium was added and mixed with the bottle contents. Heating at 50° C. continued for 40 minutes.

The polymerization was then terminated by injecting 2 ml of ethanol and 0.05g of di-t-butyl-4-methylphenol (a polymer stabilizer) into the rubber cement. The polymer was isolated by removing the volatile materials by steam distillation and the vinyl content was determined by infrared spectroscopy. The results are shown in Table I.

TABLE I

| Illustrative Embodiment | R | $R_1$ | $R_2$ | Vinyl Content % mol as Concentration of Modifier (ppm) | | | |
|---|---|---|---|---|---|---|---|
| | | | | 100 | 200 | 300 | 400 |
| II | Ethylene | Ethyl | H | 9 | 15 | 19 | 26 |
| III | Ethylene | Ethyl | Methyl | 13 | 16 | 19 | 26 |
| IV | Methylethylene | Ethyl | Methyl | 12 | 14 | 19 | 26 |
| V | Ethylethylene | Ethyl | Methyl | 12 | 14 | 18 | 24 |
| VI | Ethylene | Ethyl | Phenyl | 10 | 12 | 14 | 18 |
| VII | Trimethylene | Ethyl | Methyl | 10 | 11 | 13 | 16 |
| VIII | 1-me-tetramethylene | Ethyl | Methyl | 10 | 11 | 12 | 15 |
| IX | Tetramethylene | Ethyl | Methyl | 42 | 46 | 53 | 59 |
| X | Ethylene | Methyl | Methyl | 10 | 11 | 13 | 20 |
| XI | Ethylene | n-Butyl | Methyl | 9 | 11 | 14 | 19 |

Illustrative Embodiment XII

The procedure of Illustrative Embodiment IX was repeated except that the polymerization was run at 10° C., 35° C., 50° C. and 60 ° C. instead of just at 50° C. The resulting vinyl contents are shown in Table II.

TABLE II

| Temperature, °C. | Vinyl Content (% mol) as function of Modifier Concentration (ppm) | | | |
|---|---|---|---|---|
| | 100 | 200 | 300 | 400 |
| 10 | 58.8 | 59.2 | 60.2 | 61.5 |
| 35 | 41.1 | 51.1 | 56.7 | 60.9 |
| 40 | 35.9 | 46.9 | 54.0 | 58.3 |
| 50 | 36.5 | 42.5 | 49.2 | 55.8 |
| 60 | 22.9 | 32.5 | 42.0 | 43.1 |

Illustrative Embodiment XIII

A coupled, random styrene-butadiene branched copolymer was produced in a nitrogen-purged 500 ml serum bottle by heating at 50° C. for 2.5 hours a mixture of 9.5g styrene, 22.18 1,3 -butadiene, 250 ml cyclohexane, 0.4 mmol sec-butyllithium and 450 ppm (based on total mixture) of 2-ethoxy-2-methyl-1,3-dioxepane. Diethyl adipate was then added in a molar ratio to sec-butyllithium of 4:1 and the heating was maintained for another 30 minutes. The polymer was analyzed before and after coupling by gel permeation chromatography to determine peak molecular weights and the coupling efficiency. The vinyl content and the styrene content of the copolymer were determined by infrared chromatography. The peak molecular weight (X $10^{-3}$) before coupling was 91 and the peak molecular weights after coupling were 329,259 and 181. The coupling efficiency was 61%, the vinyl content was 40% by mol and 30% by mol of styrene was incorporated into the polymer.

Illustrative Embodiment XIV–XVI

Random styrene-butadiene copolymers were produced by contacting varying amounts of styrene and butadiene in a nitrogen-purged serum bottle with varying amounts of sec-butyllithium and 2-ethyl-2-methyl-1,3-dioxepane as modifier. The polymerizations were conducted over a 1.75-minute period at 60° C. to show the randomizing effect of the initiator on the polymerization. The reaction was then terminated by addition of ethanol. The polymers so obtained were subjected to infrared analysis to determine vinyl and styrene content. The results are shown in Table III

TABLE III

| Illustrative Embodiment | Styrene g | Butadiene g | BuLi, mmol | Modifier ppm | Conversion % | Vinyl Content % mol | Styrene Content* % mol |
|---|---|---|---|---|---|---|---|
| XIV | 9.70 | 22.64 | 0.50 | 100 | 11.1 | 20.5 | 7.9 |
| XV | 8.73 | 20.36 | 0.50 | 350 | 7.9 | 38.5 | 16.7 |
| XVI | 9.21 | 21.49 | 0.59 | 600 | 19.8 | 41.9 | 18.5 |

*In the absence of modifier, the styrene content was 2.5% mol.

Illustrative Embodiment XVII

A coupled styrene-butadiene-styrene block copolymer was produced by heating at 60° C. in a 10-liter stainless steel reactor 6 liters of cyclohexane and 295 g styrene. Polymerization was initiated by adding 26 mmol of sec-butyllithium. Heating was continued until polymerization was complete in about 1 hour. Subsequently, 3 ml of 2-ethoxy-2-methyl-1,3-dioxacyclohexane was added which was then followed by gradual addition of 705 g butadiene over 10 minutes. Heating was continued about 2 hours to obtain complete butadiene polymerization. Dibromoethane, 13 mmol, was then added and coupling of the polymer species was achieved over 0.5 hour. The polymer was isolated by steam coagulation and was dried at 50° C. in an oven. The polymer was analyzed before and after coupling by the procedure of Illustrative Embodiment XIII. The peak molecular weight (X $10^{-3}$) before coupling was 49.4 and after coupling was 103.3. The coupling efficiency was 81%, the vinyl content was 56% mol and the styrene incorporated was 29.5% mol.

What is claimed is:

1. In the process for the production of a conjugated alkadiene-based polymer of increased vinyl content by polymerizing conjugated alkadiene under polymerization conditions in the presence of a hydrocarbon reaction diluent, an organoalkali metal polymerization initiator and a structure modifier, the improvement of using as the structure modifier a compound of the formula

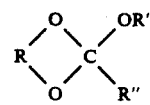

wherein R is an alkylene bridging group of up to 10 carbon atoms inclusive with from 2 to 4 carbon atoms inclusive in the bridge, R" is alkyl of up to 10 carbon atoms inclusive, and R" is hydrogen or hydrocarbyl of up to 10 carbon atoms inclusive.

2. The process of claim 2 wherein the structure modifier is provided in an amount from about 10 ppm to about 1000 ppm based on total weight of alkadiene and diluent.

3. The process of claim 2 wherein R is 1,4-butylene.

4. The process of claim 3 wherein R" is ethyl.

5. The process of claim 4 wherein R" is methyl.

6. In the process of producing a homopolymer of butadiene or isoprene of increased vinyl content by polymerizing butadiene or isoprene under polymerization conditions in the presence of a hydrocarbon reaction diluent, an alkyllithium polymerization initiator and a structure modifier, the improvement of using as the structure modifier a compound of the formula

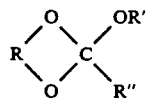

wherein R is an alkylene bridging group of up to 10 carbon atoms inclusive with from 2 to 4 carbon atoms inclusive in the bridge, R' is alkyl of up to 10 carbon atoms inclusive, and R" is hydrogen or hydrocarbyl of up to 10 carbon atoms inclusive.

7. The process of claim 6 wherein the structure modifier is provided in a quantity from about 50 ppm to about 850 ppm based on total weight of butadiene or isoprene and diluent.

8. The process of claim 7 wherein R is 1,4-butylene.

9. The process of claim 8 wherein R' is ethyl.

10. The process of producing a copolymer of conjugated alkadiene and vinylaromatic hydrocarbon of increased vinyl content under polymerization conditions in the presence of a hydrocarbon reaction diluent, an alkyllithium polymerization initiator and a structure modifier, the improvement of using as structure modifier a compound of the formula

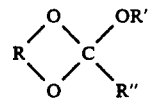

wherein R is an alkylene bridging group of up to 10 carbon atom inclusive with from 2 to 4 carbon atoms inclusive in the bridge, R' is alkyl of up to 10 carbon atoms inclusive, and R" is hydrogen or hydrocarbyl of up to 10 carbon atoms inclusive.

11. The process of claim 10 wherein the structure modifier is employed in an amount from about 50 ppm to about 850 ppm based on total alkadiene and diluent.

12. The process of claim 11 wherein R is 1,3-butylene.

13. The process of claim 12 wherein R' is ethyl.

14. The process of claim 13 wherein R" is methyl.

* * * * *